(12) United States Patent
Large et al.

(10) Patent No.: US 8,208,145 B2
(45) Date of Patent: Jun. 26, 2012

(54) ANALYTICAL APPARATUS

(75) Inventors: Timothy Andrew Large, Dunmow (GB); Graham Eric Gifford, Toft (GB); Stephen Paul Marriott, Grey (GB)

(73) Assignee: Biochrom Limited, Cambridge (GB)

( * ) Notice: Subject to any disclaimer, the term of this patent is extended or adjusted under 35 U.S.C. 154(b) by 479 days.

(21) Appl. No.: 12/304,225

(22) PCT Filed: Jun. 8, 2007

(86) PCT No.: PCT/GB2007/002129
§ 371 (c)(1),
(2), (4) Date: Jun. 30, 2009

(87) PCT Pub. No.: WO2007/144583
PCT Pub. Date: Dec. 21, 2007

(65) Prior Publication Data
US 2010/0060879 A1  Mar. 11, 2010

(30) Foreign Application Priority Data

Jun. 14, 2006 (GB) .................................. 0611701.4
Nov. 27, 2006 (GB) .................................. 0623574.1

(51) Int. Cl.
*G01J 3/00* (2006.01)
*G01N 21/01* (2006.01)
*G01N 21/25* (2006.01)

(52) U.S. Cl. ............ 356/436; 356/51; 356/440; 356/246

(58) Field of Classification Search .................... 356/51, 356/440, 445, 300–301, 244, 246, 432–437; 436/165–166, 174, 518, 525; 435/287.2, 435/4–7, 7.1, 7.2; 422/58, 61, 82.01, 99, 422/102, 104
See application file for complete search history.

(56) References Cited

U.S. PATENT DOCUMENTS

| 3,518,009 A | | 6/1970 | Shamos | |
|---|---|---|---|---|
| 4,761,381 A | * | 8/1988 | Blatt et al. | 436/165 |
| 5,209,904 A | * | 5/1993 | Forney et al. | 422/73 |

(Continued)

FOREIGN PATENT DOCUMENTS

EP  1652582 A  5/2006

(Continued)

OTHER PUBLICATIONS

Search report in GB0623574.1, dated Mar. 22, 2007.

*Primary Examiner* — Sang Nguyen
(74) *Attorney, Agent, or Firm* — Barnes & Thornburg LLP

(57) ABSTRACT

Apparatus for analysing a liquid sample (194) comprises beam generating means (1) for generating electromagnetic radiation, detector means (8) for detecting electromagnetic radiation from the beam generating means after the radiation has interacted with the sample, and sample retaining means (10) for releasably retaining sample in the path of the beam. The sample retaining means comprises a hydrophobic surface (for example, a coating on a plate 118) on which the sample is, in use, supported. There is also disclosed a method of performing photometric or spectrophotometric analysis of a liquid sample by sandwiching samples between two opposed hydrophobic support surfaces, passing a beam of electromagnetic radiation through one of the surfaces and then through the sample, and analysing the beam after it has passed through the sample.

29 Claims, 18 Drawing Sheets

U.S. PATENT DOCUMENTS

| | | | | |
|---|---|---|---|---|
| 5,503,803 A * | 4/1996 | Brown | | 422/547 |
| 6,066,448 A * | 5/2000 | Wohlstadter et al. | | 435/6.11 |
| 6,197,494 B1 * | 3/2001 | Oberhardt | | 435/4 |
| 6,288,390 B1 * | 9/2001 | Siuzdak et al. | | 250/288 |
| 6,486,947 B2 * | 11/2002 | Modlin et al. | | 356/246 |
| 6,600,558 B2 * | 7/2003 | Ueno et al. | | 356/246 |
| 6,628,382 B2 | 9/2003 | Robertson | | |
| 6,809,826 B2 | 10/2004 | Robertson | | |
| 7,033,542 B2 * | 4/2006 | Archibald et al. | | 422/82.09 |
| 7,204,139 B2 * | 4/2007 | Takayama | | 73/204.26 |
| 7,244,349 B2 * | 7/2007 | Vogel et al. | | 205/777.5 |
| 7,901,875 B2 * | 3/2011 | Stiene | | 435/4 |
| 2005/0110990 A1 * | 5/2005 | Koo et al. | | 356/301 |
| 2005/0196747 A1 * | 9/2005 | Stiene | | 435/4 |
| 2005/0208539 A1 * | 9/2005 | Vann et al. | | 435/6 |
| 2006/0269453 A1 * | 11/2006 | Roitman et al. | | 422/102 |

FOREIGN PATENT DOCUMENTS

| | | |
|---|---|---|
| JP | 2003294610 A1 | 9/1992 |
| JP | 04249736 A | 10/2003 |
| WO | WO-03/034026 A | 4/2003 |
| WO | WO-2005/114146 A1 | 12/2005 |
| WO | WO-2006/005881 A | 1/2006 |
| WO | WO-2006/005881 A1 | 1/2006 |

* cited by examiner

ANALYTICAL APPARATUS

FIELD OF THE INVENTION

This invention relates to apparatus for analysing a liquid sample, and to a method of performing photometric or spectrophotometric analysis of a liquid sample.

BACKGROUND TO THE INVENTION

The invention is of particular application to the analysis of low volume liquid samples, for example of volumes of five microlitres or less, such as would be used in the quantitative analysis of aqueous samples of DNA created in the laboratory. Since such DNA is a valuable resource, only a very small sample is usually available for assessment.

Typically, the analysis of a DNA sample involves passing a beam of light through the sample and measuring the amount of light absorbed at different wavelengths. Since the DNA has different absorbence characteristics from other proteins, the measurements can be used to provide a ratio of the concentration of DNA to that of other proteins in the sample.

U.S. Pat. No. 6,628,382 shows apparatus in which a sample in the form of a small volume liquid drop is sandwiched between two opposed anvil surfaces. The surfaces are moved together to compress the drop, at which point a first measurement is taken by passing light through the drop. The surfaces are then moved apart so as to draw the drop into a thin, concaved column in which condition a further measurement is taken by passing light axially along the column. After the measurements have been taken, the droplet cannot be fully retrieved since it will leave residues on the anvil surfaces which will need to be thoroughly cleaned in order to avoid problems of cross contamination with droplets subsequently placed in the apparatus. In addition, any dust in the sample droplet will affect the accuracy of the apparatus and the droplet, when drawn into the column, can lose significant amounts of liquid through evaporation and be affected by photobleaching caused by the ultraviolet light used in the measurement. These factors also affect the accuracy of the apparatus.

The invention seeks to avoid or at least mitigate one or more of the above-mentioned problems.

SUMMARY OF THE INVENTION

According to a first aspect of the invention, there is provided apparatus for analysing a liquid sample, the apparatus comprising generating means for generating electromagnetic radiation, detector means for detecting electromagnetic radiation from said generating means after the electromagnetic radiation has interacted with the sample and sample retaining means for releasably retaining the sample in the part of the beam, wherein the sample retaining means comprises a hydrophobic surface on which the sample is, in use, supported.

Since the sample is supported on a hydrophobic surface, it is a relatively straightforward matter to retrieve substantially all of the sample after the measurement has been made, for example a pipette could be used to remove the sample, the surface tension of the liquid of the sample assisting in the drawing of the whole sample into the pipette. Since the surface is hydrophobic, wetting of the surface by the sample will not occur so that the surface is clean after use. This reduces the risk of cross contamination between successive samples being analysed in the apparatus.

Preferably, the apparatus is operable to generate a beam of electromagnetic radiation, and to define a path for said beam which path passes through at least a part of a sample being analysed.

The electromagnetic radiation may, for example, be ultraviolet light.

Preferably, the surface is one of a pair of such surfaces between which, in use, a sample being analysed is sandwiched.

This enables a sample to be constrained in such a way that the length of the path of the electromagnetic radiation through the sample is accurately defined and reproduced from one sample to the next.

Preferably, at least one of the surfaces is moveable so that the surfaces have an open condition in which a sample may be applied to or removed from at least one of the surfaces, and a closed condition in which the sample is sandwiched between the two surfaces.

Preferably, the surfaces are positioned one above the other and are substantially parallel to each other when in the closed condition.

Thus, insertion of the sample into the apparatus simply involves placing the sample on the lower surface when the surfaces are in the open condition, and the sample can subsequently be retrieved simply by being removed from the lower surface (substantially no residue remaining on the upper surface in view of its hydrophobic nature).

Preferably, the upper of said surfaces is mounted on a pivotal arm assembly so arranged that pivoting of the arm assembly moves the upper surface to achieve said movement between the open and closed conditions.

Such an assembly is convenient to use and can be of a robust and durable construction.

Preferably, the apparatus includes an interlock operable to permit operation of the beam generating means only when the surfaces are in their closed position.

This avoid the risk of the beam generating means operating when the surfaces are not in their closed condition and thus reduces the risk of inadvertent exposure of the user to radiation from the beam generating means.

Preferably, the interlock comprises a magnet and a magnetic switch, which are brought into and out of operative engagement with each other by the opening and closing of the surfaces.

It will be appreciated that "operative engagement" does not necessarily require contact of the magnet and the switch: such engagement will be achieved if the magnet is sufficiently close to the switch to change the state of the latter (from closed to open or vice versa).

The magnet may to advantage be fixed relative to one of the surfaces, the switch being fixed relative to the other.

The switch conveniently comprises a "Hall Effect Sensor".

Preferably, the surfaces are constituted by hydrophobic coatings on upper and lower members.

Preferably, the lower member is transparent to allow the passage into the sample of the beam from the beam generating means, said beam being incident on the lower member from underneath.

The lower member preferably comprises a plate.

The apparatus may to advantage include an overhead reflector for reflecting the beam that has passed through the sample back to a region beneath the underside of the lower member.

Preferably, the reflector comprises a prism.

A face of the prism may constitute the upper surface, but the prism is preferably spaced from the member on which the upper surface is provided.

The upper surface is conveniently constituted by a hydrophobic coating on an upper transparent plate situated beneath said reflector.

Preferably, the plates are removable. To that end, the plates may, for example, be releasably snap-fitted into the apparatus.

This allows for relatively swift and easy removal and replacement of the plates if the hydrophobic coatings become worn.

The beam generating means and detector may each to advantage include a respective light guide means, respectively for emitting the beam towards the sample and receiving the beam transmitted through the sample. Both light guide means are preferably terminated below the lower surface.

Each light guide means may conveniently comprise a respective optical fibre.

The apparatus may to advantage include a moveable stop for defining a minimum distance between the surfaces, when in their closed condition, and drive means for extending and/ or retracting. Automatically to vary the distances in accordance of a succession of measurements performed on the sample.

Preferably, the distance between the surfaces, when in their closed condition, is not more than 0.1 mm and is preferably not more than one millimeter. In this case, the diameter of the beam is preferably of the order of 1-5 millimeters, more preferably, 1.6 millimeters. Since the drop is sandwiched between two hydrophobic surfaces, it is formed into an oblate spheroid which can have a larger diameter than a concaved column. This allows a larger diameter of beam to be passed through the sample and thereby reduces the possible errors in the measurements caused by dust in the sample (since each particle of dust represents a smaller percentage of the total cross-sectional area being irradiated).

Preferably, the plate includes a well located in the path of electromagnetic radiation through the plate.

The well helps to centre the sample in the desired position, over the well, on the plate.

The well may to advantage be defined by a further coating being situated underneath the hydrophobic coating, and having an aperture which defines the well.

The coating may be opaque, and may for example be grey or black ink printed onto the plate.

According to a second aspect of the invention, there is provided a method of performing photometric or spectrophotometric analysis of a liquid sample of a volume not more than five microlitres, the steps of sandwiching the sample between two opposed hydrophobic support surfaces, passing a beam of electromagnetic radiation through one of the surfaces and through the sample and analysing the beam after it has passed through the sample.

Preferably, the beam, after having passed through the sample, is reflected towards a detector for analysing the beam.

The reflection is preferably achieved using a prism situated on the opposite side of one of the surfaces from the sample.

Preferably, the method involves passing the beam vertically upwards through a lower surface, through the sample, through the upper surface and then reflecting the beam back down to a region below the lower surface, at which a detector is located.

Preferably the beam has a diameter of the order of 1-5 millimeters and the ample has a cross sectional area which is at least as large as that of the beam.

BRIEF DESCRIPTION OF THE DRAWINGS

The invention will now be described, by way of example only, with reference to the accompanying drawings in which.

DETAILED DESCRIPTION

Figure 1:
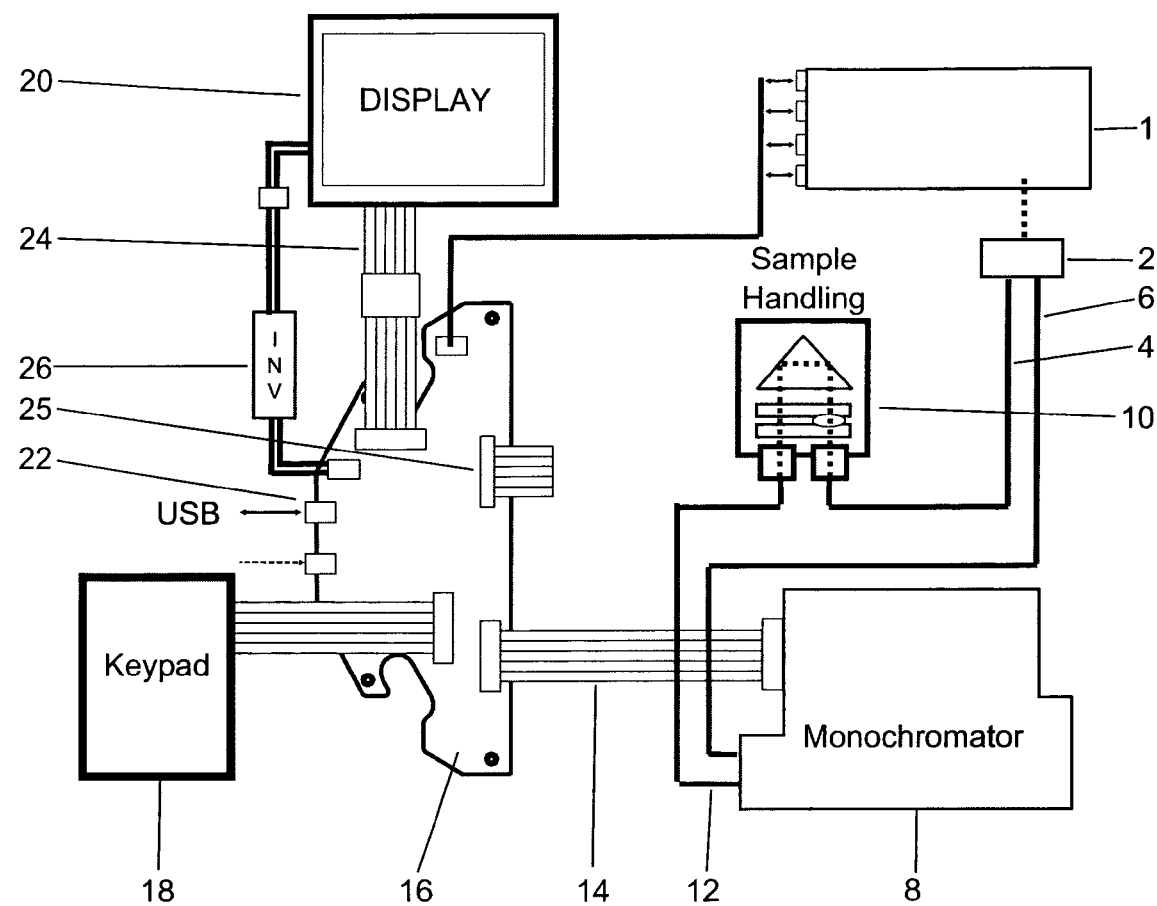
FIG. 1 is a schematic view of apparatus in accordance with the invention for performing the method also in accordance with the invention.
Figure 2:
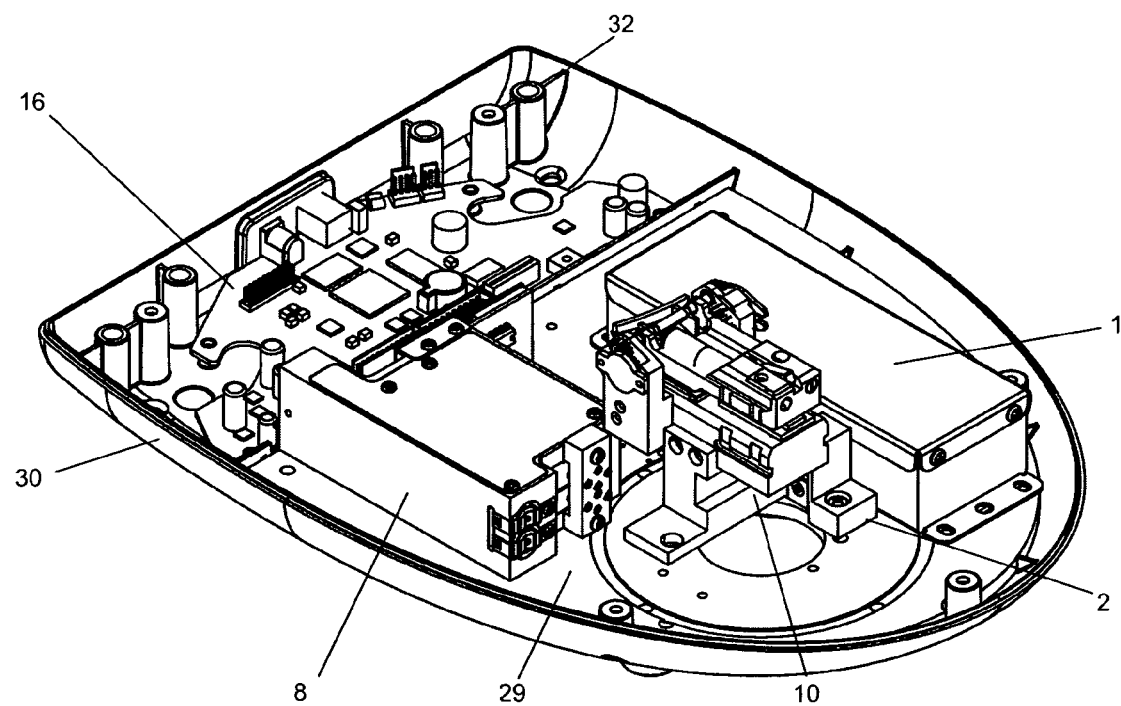
FIG. 2 is an isometric view of the assembled apparatus (with its top cover removed)

With reference to FIGS. 1 and 2, the apparatus hereinbelow described is a spectrophotometric analyser of liquid samples (containing DNA and other proteins) supplied to the analyser in droplets of a volume of five microlitres or less. The apparatus comprises a xenon lamp module 1 that acts as means for generating an electromagnetic beam supplied to a beam splitter 2 a detector means in the form of a dual monochromator 8 and a sample handling assembly 10. The beam splitter 2 splits the beam into two further beams, each of which is fed to a respective one of two optical fibres 4 and 6. The fibre 6 is connected directly to one half of the dual monochromator 8 whilst the beam fed along the optical fibre 4 is also supplied to the monochromator 8, but via the sample handling assembly 10, in which the sample to be analysed is contained, and a further optical fibre 12 connecting the assembly 10 to said other half of the monochromator 8.

The output of the monochromator 8 is connected by cable 14 to a Printed Circuit Board (PCB) 16 that provides the electronics and associated software to control the light source in the xenon lamp module, the sample handling assembly 10 and the monochromator 8. Commands can be fed to the PCB via a keypad 18 whilst the results of the analysis conducted on the sample can be displayed on a display 20 or fed via a USB output 22 to a separate computer (not shown). Control signals for the display are fed along a cable 24 whilst the PCB also provides power for operating the display, fed to the latter via an inverter 26. As indicated at 28, the PCB also has connections for a separate printer or other type of recorder, on which the results of the analysis may also be recorded.

In FIG. 2, the various cables connecting the PCB 16 to other elements have been omitted for the sake of clarity. The various components are mounted on an aluminium plate 29 itself mounted on a base tray 30 of a plastics material. The PCB 16 is situated towards the rear of the plate 29 and tray 39 and the sample handling assembly 10 is positioned further forward and extending above the top of the tray 30. The tray 30 includes known types of fixing, such as 32 in the form of screw threaded cylindrical sockets via which a cover (also of a plastics material) can be removably attached to the tray 30. The cover, as well as improving the appearance of the apparatus, protects the apparatus from liquid spillage and provides a mounting surface for the screen and keypad. The cover is shown at 34 in FIGS. 12-14.

Figure 3:
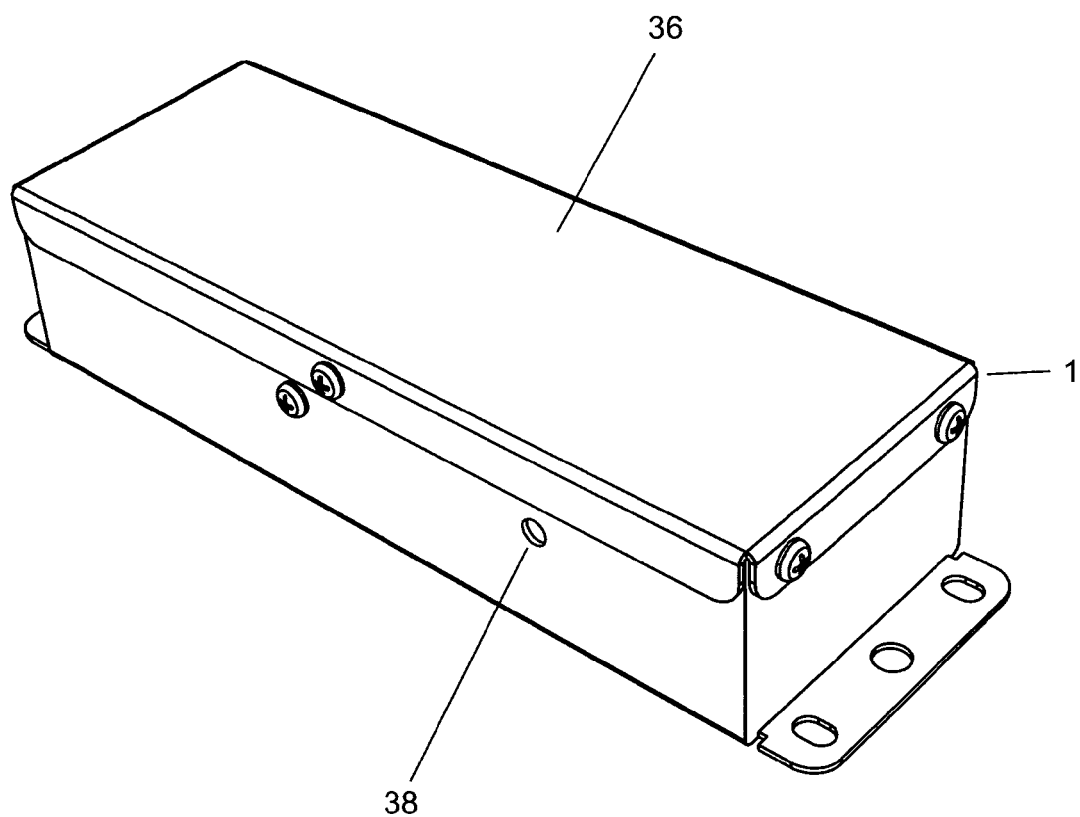
FIG. 3 is an isometric view of a light source forming part of the apparatus.

Turning to FIG. 3, the xenon lamp module 1 comprises a housing 36 which contains a pulsed xenon source running at approximately 20 Hz but generates a series of light flashes to illuminate the sample over a broad range of wavelengths, from 190 mm to 1100 mm. Light could be provided by a variety of other lamp types, for example deuterium for ultraviolet operation or a tungsten filament lamp for visible and IR (infra red) use. Power for operating the xenon lamp in the present example is supplied by the PCB 16, but the module includes power modification circuitry for supplying the correct voltage to the lamp.

Figure 5:
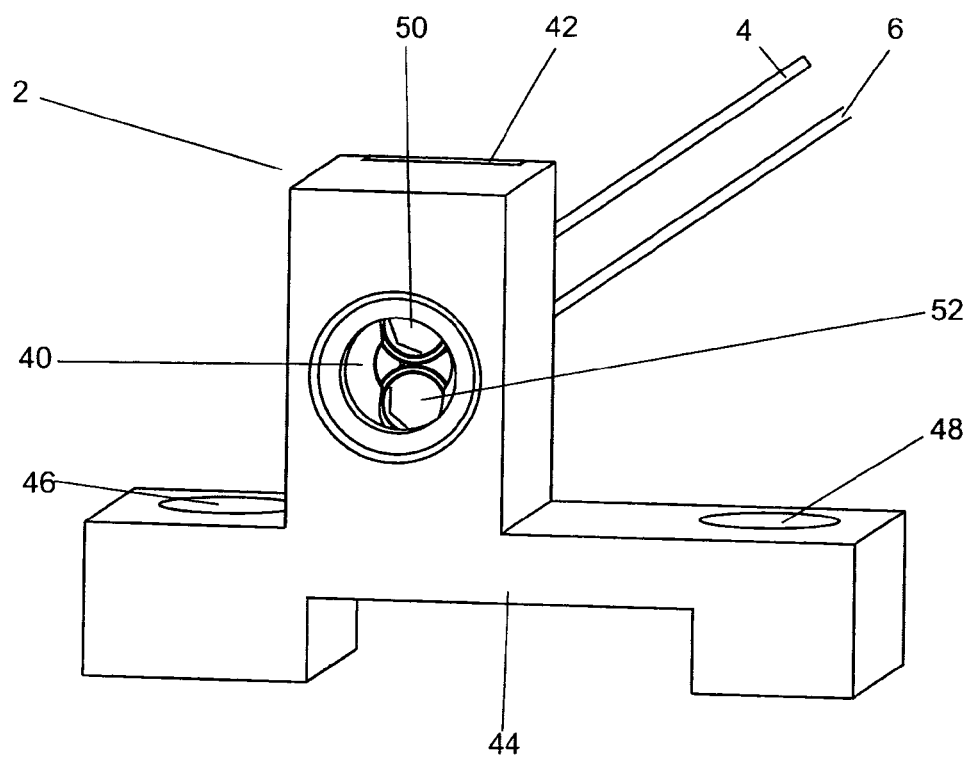
FIG. 5 is an isometric view of a beam splitter forming part of the apparatus.
Figure 6:
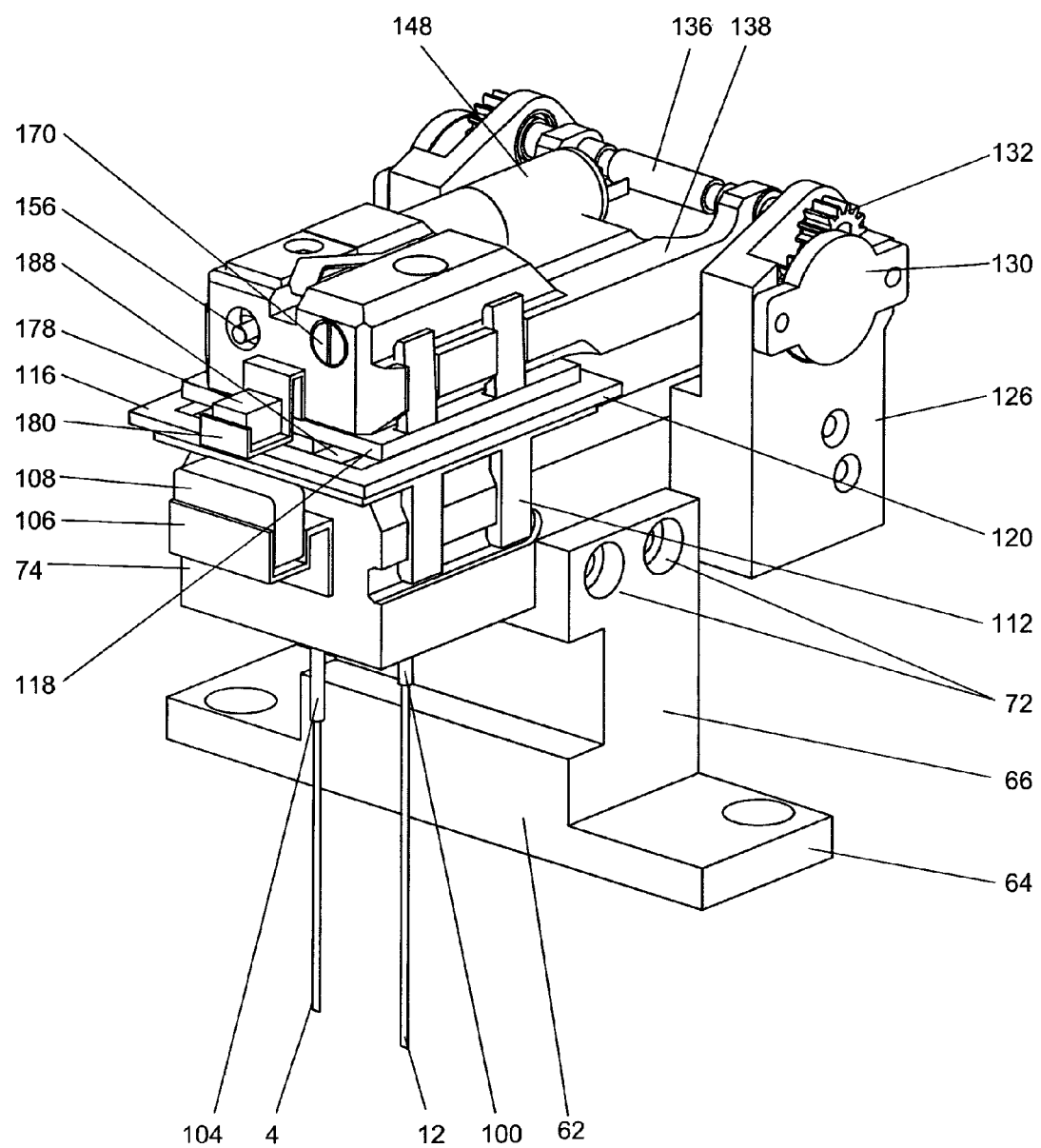
FIG. 6 is an isometric view of a sample handling assembly for the apparatus, the assembly being shown in a closed condition.
Figure 7:
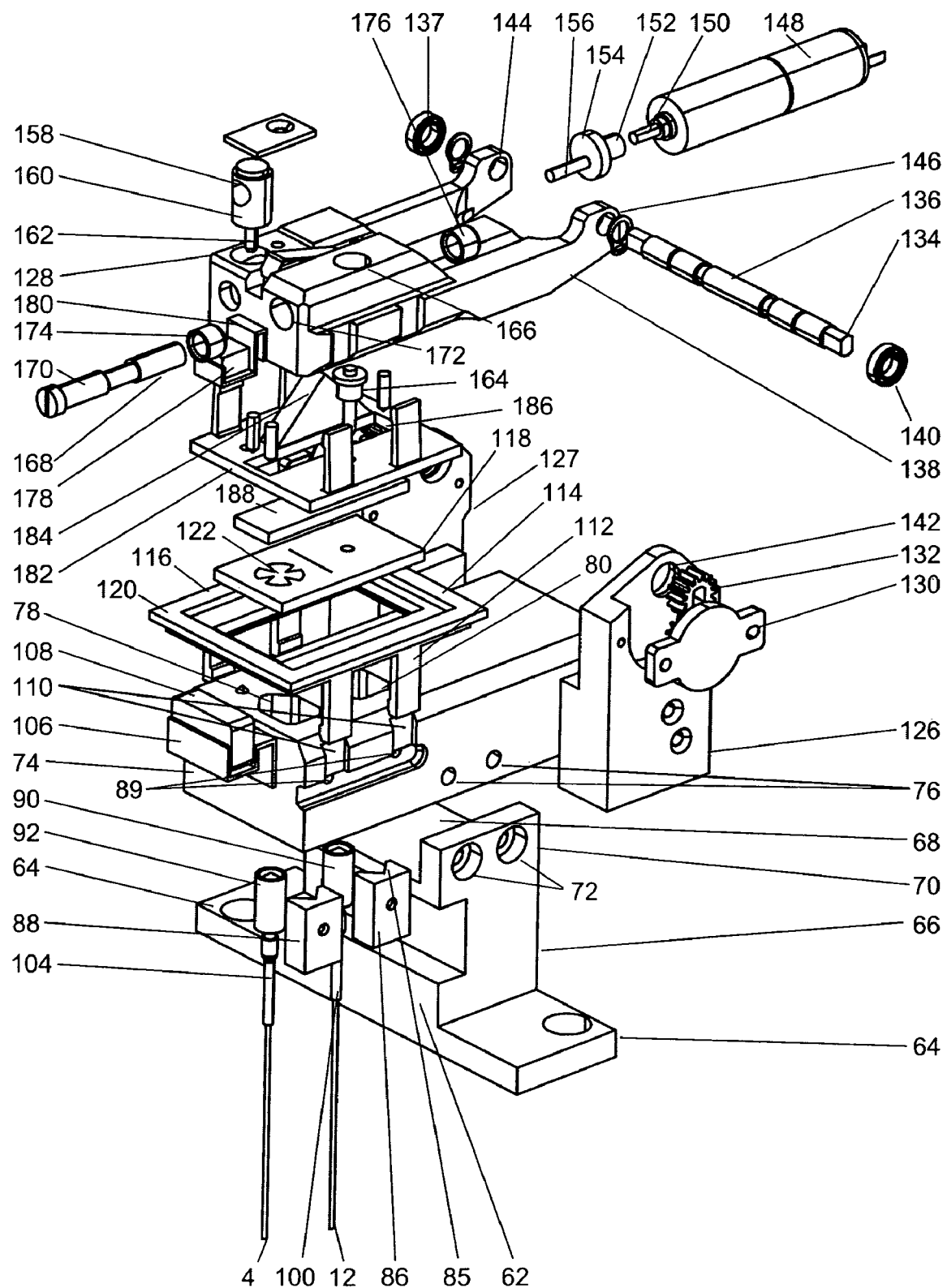
FIG. 7 is an exploded isometric view of the assembly.
Figure 8:
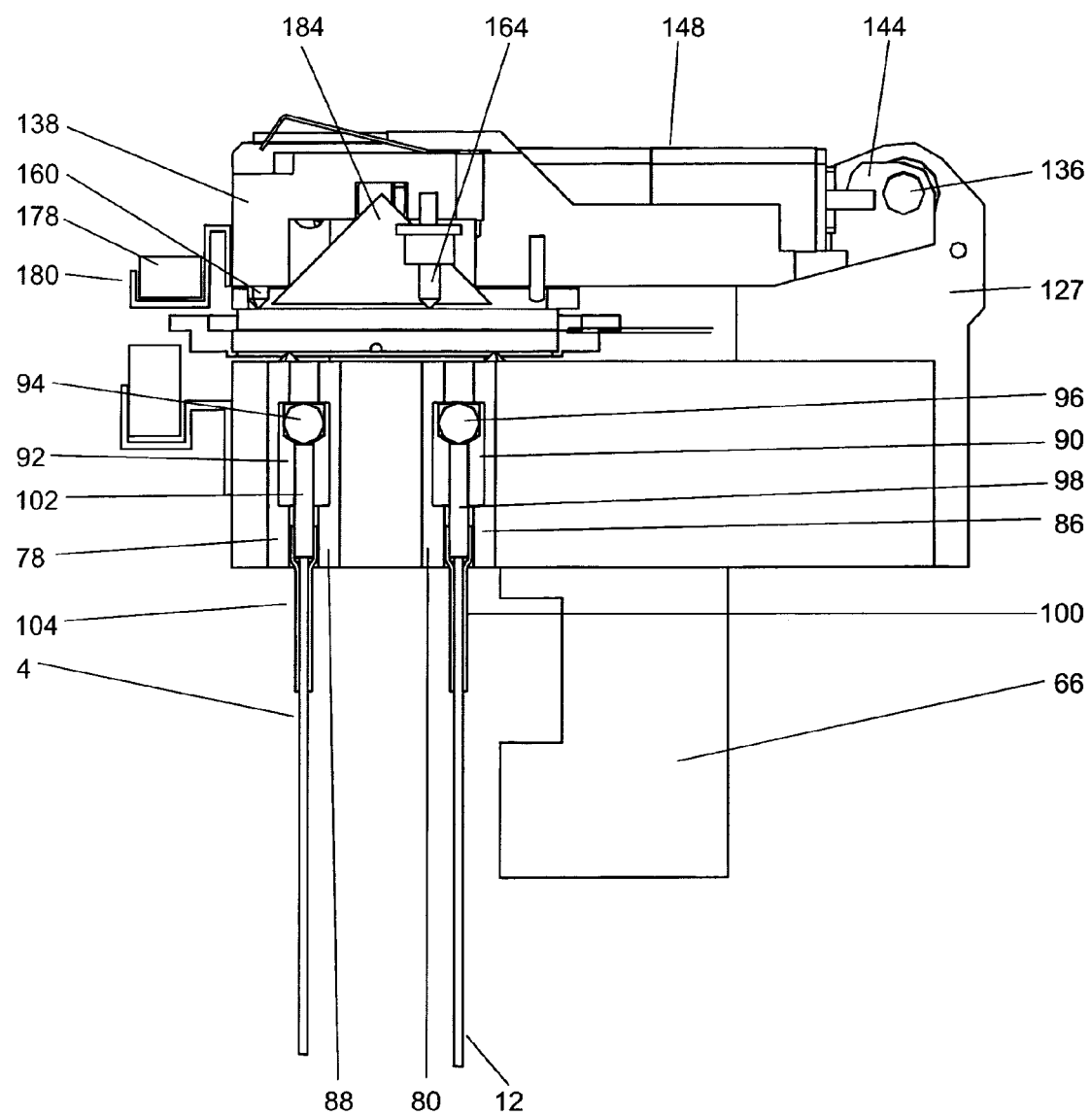
FIG. 8 is a cut away side elevation of the assembly.
Figure 9:
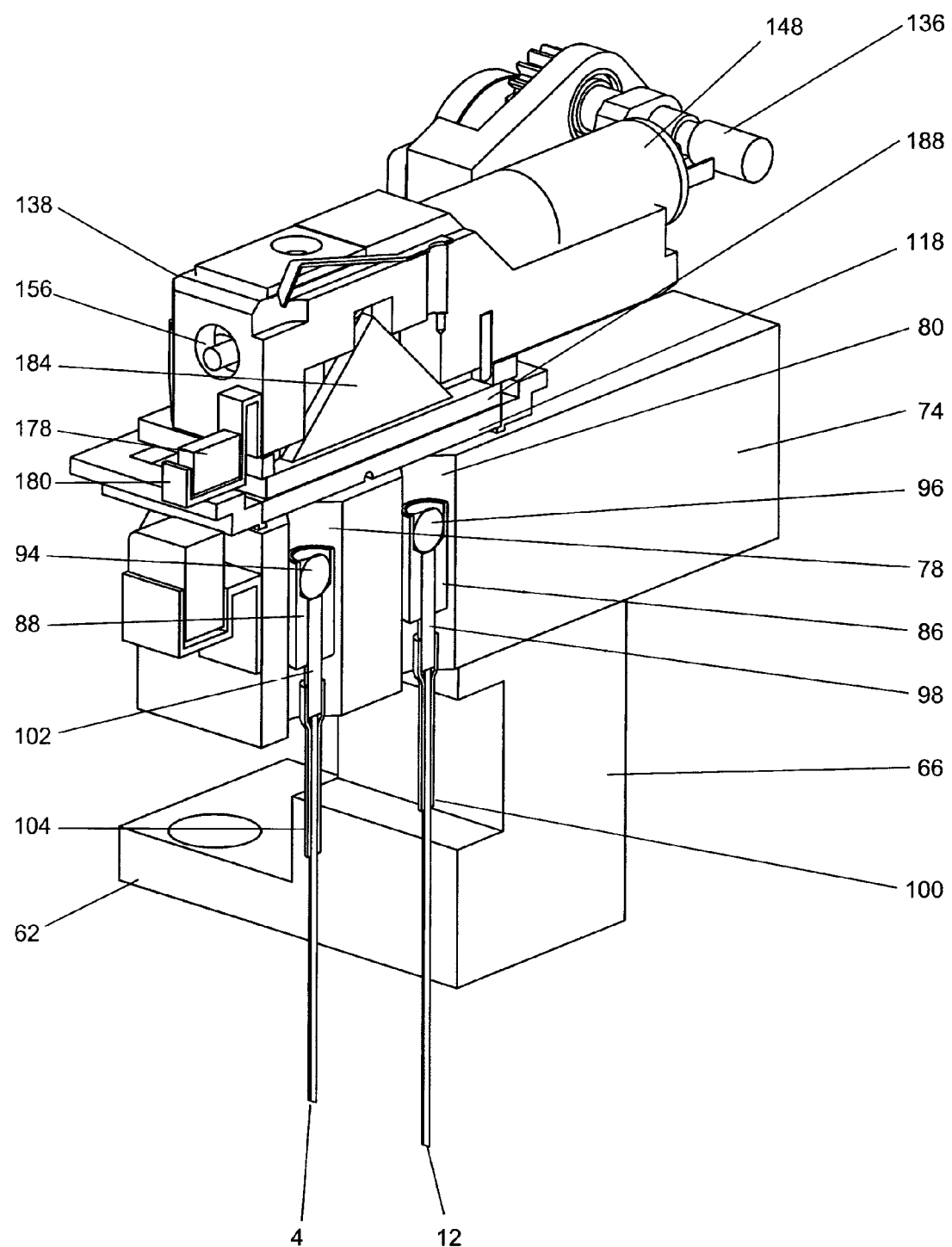
FIG. 9 is an isometric cut away view of the assembly.
Figure 10:
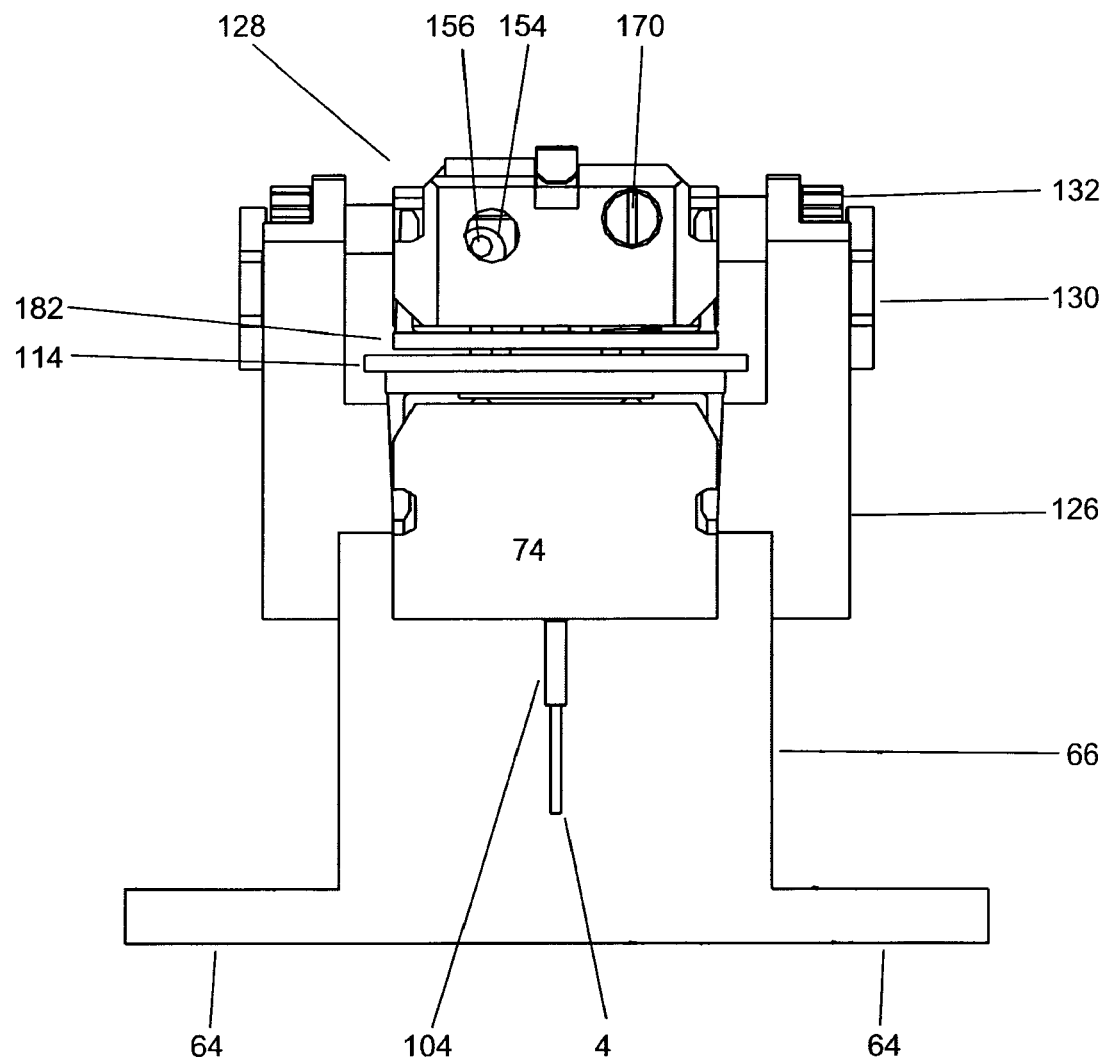
FIG. 10 is a front elevation of the assembly.

The module 1 has an output aperture 38 through which light from the xenon lamp passes into an input aperture 40 of the beam splitter 2 which is shown in more detail in FIG. 5. The aperture 40 is formed in a vertically extending rectangular block 42 which is formed integrally (from a suitable plastics material) with a base 44 provided with passages 46 and 48 for fixing the base 44 to the plate 29.

The aperture 40 is the end of a passage in the block 42, which passage also accommodates two lenses 50 and 52 optically coupled to optical fibres 4 and 6 respectively, and a condensing lens (not shown) in between the aperture and the lenses 50 and 52 and hence in the path of the beam to be split. The condensing lens collimates the incoming light from the beam, and thereby uniformly illuminates the lenses 50 and 52, thus splitting the beam between those lenses.

It will be appreciated that other types of beam splitter could be used, for example a beam splitter employing a semi-silvered mirror or a beam splitter using a mirror pattern (where the pattern is substantially smaller than the beam size).

Figure 4:
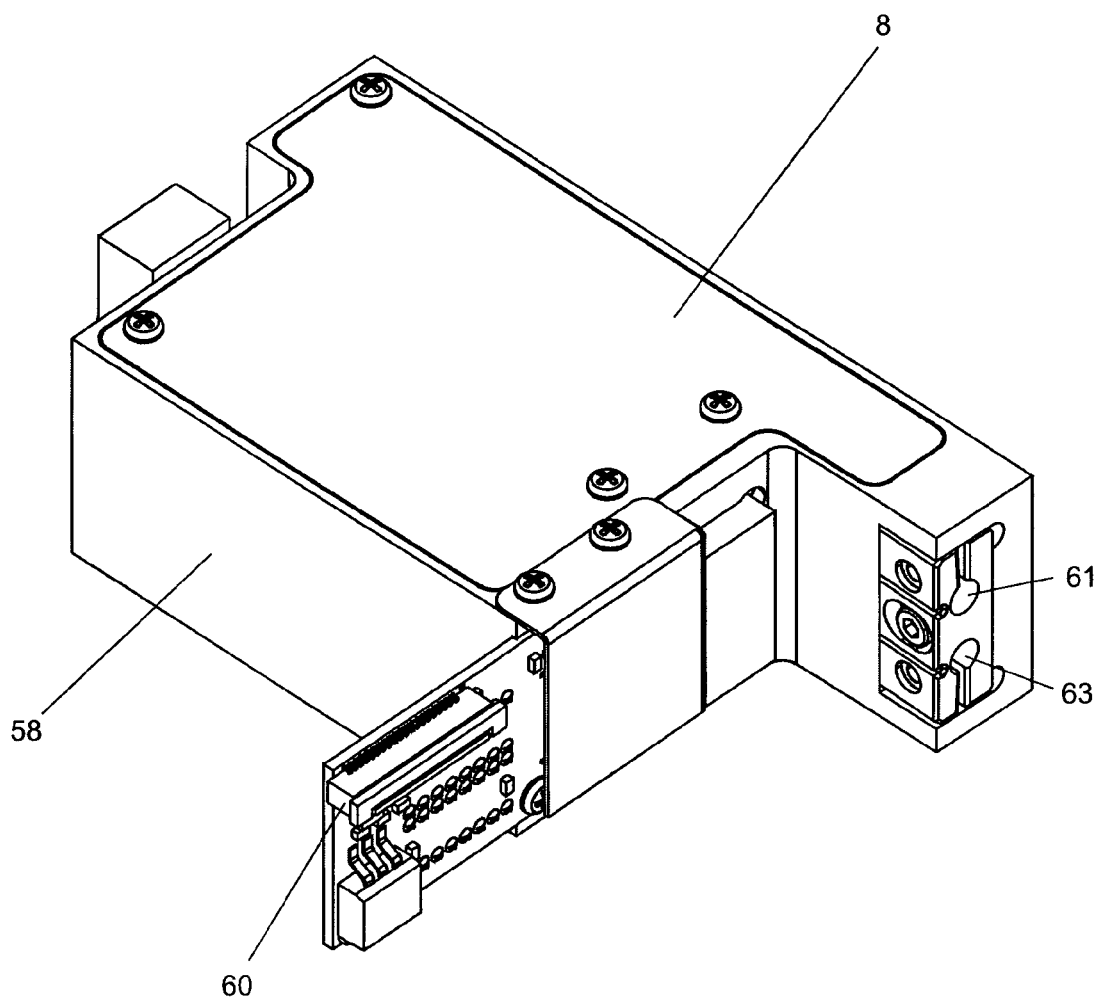
FIG. 4 is an isometric view of detector means for the apparatus.

Turning to FIG. 4, the monochromator 8 is of a known kind, that converts incoming broadband light into individual or narrow band width components, the intensity of each of which is measured by means of an appropriate detector (e.g. a CCD, photo diode array, photomultiplier or single photo diode) forming part of the monochromator. These components are contained in a housing 58, the electrical connections to the device being made via connecting board 60, whilst the inputs for the optical fibres 6 and 12 are provided at 61 and 63. The monochromator is of a type that can analyse light from the two inputs to provide two sets of spectral data that can be compared as discussed below in the description of the operation of the system. The splitting of the incoming light from each source may be achieved by any one of a number of possible means, such as interference filters, diffraction gratings or prisms. In this example, the monochromator uses diffraction gratings, and is of dual Czeny-Turner construction.

The lamp module, beam splitter, monochromator and PCB are of general types already known in the art, and have not been described in more detail. However, the sample handling assembly shown in FIGS. 6-9 differs from known arrangements in a number of important respects, and will now be described in more detail with reference to those figures.

Figure 11:
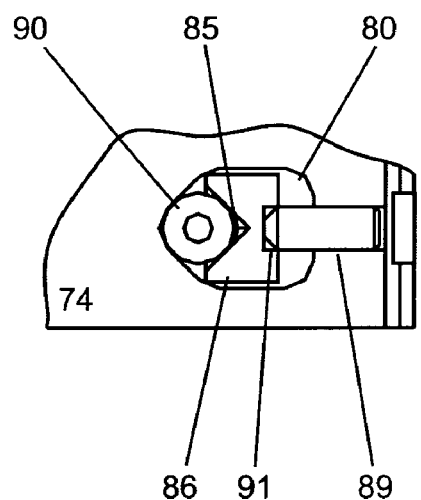
FIG. 11 is a section view (along part of the line A-A of FIG. 10) of part of the assembly.

The assembly 10 comprises a base block 62 which has a pair of opposed lower apertured lugs 64 via which the block 62 is screwed into the tray 30. A vertical support portion of the base block 62, reference 66 arises from the lugs 64 and defines a substantially horizontal support platform 68 from which a sidewall 70 rises. An identical side wall rises from the other side of the platform 68. Both sidewalls have apertures 72 through which a table 74 (having registering apertures 76) is screwed onto the base block 62. The table 74 has a pair of through bores 78 and 80 extending vertically from the bottom to the top of the table in line with its longitudinal axis. Each bore contains a respective one of two clamping blocks 86 and 88, the block 86 being shown in section plan view in FIG. 11. The block 86 includes a longitudinal V-shaped groove 85 which pushes a collar 90 against the bore 80 to clamp the collar 90 in position in the bore 80. The side of clamping block 86 opposite the groove has a circular depression 91 for receiving a screw that passes through a screw threaded hole 89 in the table 74 and can be tightened against the block to urge the latter against the collar, thereby to provide the necessary force for the clamping action.

The clamping block 88 is identical to block 86, and clamps a collar 92 in position in the same way as the block 86 clamps the collar 90.

Each collar houses a respective one of two identical sapphire ball lenses 94 and 96.

The optical fibre 12 is held against the lens 96 by means of a glass ferrule 98 which is firmly held within the collar 90. The ferrule 98 tightly holds the end of the fibre 12 which extends through the ferrule. The top end of a sheath 100 also extends into the base of the ferrule 98 to help secure the fibre in the ferrule. A similar arrangement of a ferrule 102 and sheath 104 connects with the lens 94 to the fibre 4.

The front edge of the table 74 carries a mounting bracket 106 in which a magnet 108 is mounted. A pair of vertical slots 110 extend along part of one side of the Table 74 as far as a horizontal recess in which the holes 89 are accommodated. An identical arrangement of vertical slots and a horizontal slot are provided on the opposite side of the table 74. The slots each accommodate a respective tang such as tang 112 which is vertical and forms part of a lower sample plate holder 114. The lower end of each tang 112 carries on its inner surface a latching formation that releasably engages in the horizontal recess in which the holes 89 are provided (or the corresponding slot on the opposite side of the table 74) so that the holder 114 can be releasably snap-fitted onto the table 74.

The holder of 114 has a rectangular peripheral frame 116 in which a glass plate 118 is mounted. The frame 116 includes an outer peripheral ridge 120, the inner edge of which is, in use, spaced from the plate 118 so that there is defined between the plate and the ridge a trough into which excess sample liquid may fall if the user has applied too much sample to the plate 118. The plate 118 carries on its upper surface a hydrophobic coating (for example, DuPont's Teflon AF and a cross marking 122 to indicate the desired position for the sample droplet.

The end of the table 74 opposite the bracket 106 is attached to two mounting blocks 126 and 127 via which an upper arm assembly 128 is pivotally mounted on the table 74. The assembly 128 is also attached to a rotary dashpot 130 which provides damping for rotational movement of a cog 132 which meshes with a corresponding cog on the dashpot 130. The cog 132 has a rectangular central aperture into which a correspondingly shaped end portion 134 of a hinge pin 136 extends. The other end portion of the hinge pin 136 is similarly shaped, and engages an identical cog and dashpot arrangement attached to the block 127. Thus the hinge pin 136 is rotationally keyed to the dashpots. However, the hinge pin is also mounted on the blocks on ball race bearings 137 and 140, each lining a respective aperture (such as aperture 142) in one of the blocks 126 and 127. Accordingly, the hinge pin 136 can rotate on the ball race bearings 137 and 140 about its elongate access, and hence is rotatable relative to the blocks 126 and 127 and thus the table 74.

The upper arm assembly includes an upper carrier arm 138 having apertured fixing lugs 144 and 146 through which the pin 136 passes, and at which the pin 136 is rotationally fixed to the arm 138. Accordingly, the carrier arm 138 is pivotable relative to the table 74 about the axis defined by the pin 136.

The carrier arm 138 includes a passage which runs substantially perpendicular to the pivot access and is situated adjacent to the side of the carrier arm 138 in which the lug 144 is provided. This passage accommodates the forward end of drive means comprising an electric motor/gear box assembly 148 having a mechanical output 150 connected to an actuator 152. The actuator fits over the output 150, and includes a guide disc 154 from which an eccentric rod 156 projects forwardly. The disc 154 provides axial location of the actuator 152 within the passage in the carrier arm 138, whilst allowing the actuator to rotate in response to the operation of the motor 148. The rod 156 engages in a diametric through bore 158 in a cylinder 160 from the bottom end of which a stop in the form of a pin 162 extends. The cylinder 160 is a sliding fit in a vertical bore in the arm 138, so that the operation of the motor 148 can move the pin 162 vertically from a position in which it protrudes beneath the arm 138 to engage the plate 118 into a position in which the pin is substantially fully retracted into the arm 138.

A further spacer pin 164 is partially accommodated in a vertical bore 166 in the arm 138 and is upwardly biased by means of a spring (not shown). An actuator comprising a cam 168 mounted on a screwhead 170 extends into a horizontal bore 172 from the front of the arm 138, and through the bore 166, so that the cam 168 bears against the top of the pin 164. Accordingly, the degree of extension of the pin 164 can be manually adjusted by means of the screw head 170 accessible from the front of the arm 138. The actuator passes through bearing races 174 and 176 which enable the actuator to rotate about its elongate access in the bore 172.

At the front of the arm 138 there is provided a Hall Effect sensor 178 mounted in a bracket 180, and arranged to co-operate with the magnet 108 so that the xenon lamp module 1 is prevented from operating unless the magnet and sensor are close together (i.e. unless the upper arm 138 is in the closed position).

Figure 12:
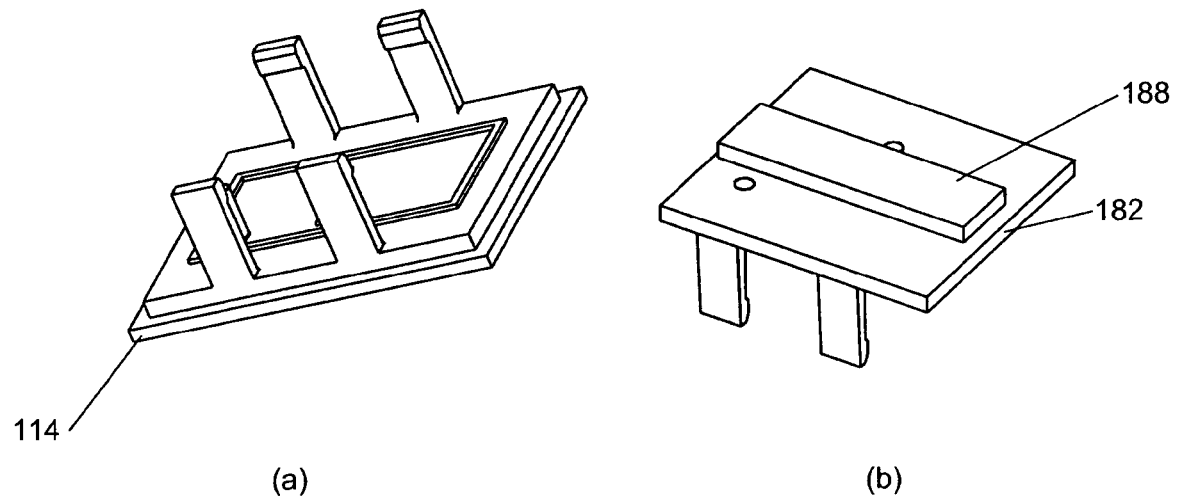
FIGS. 12a and 12b are isometric views of two plate holders of the assembly.
Figure 13:
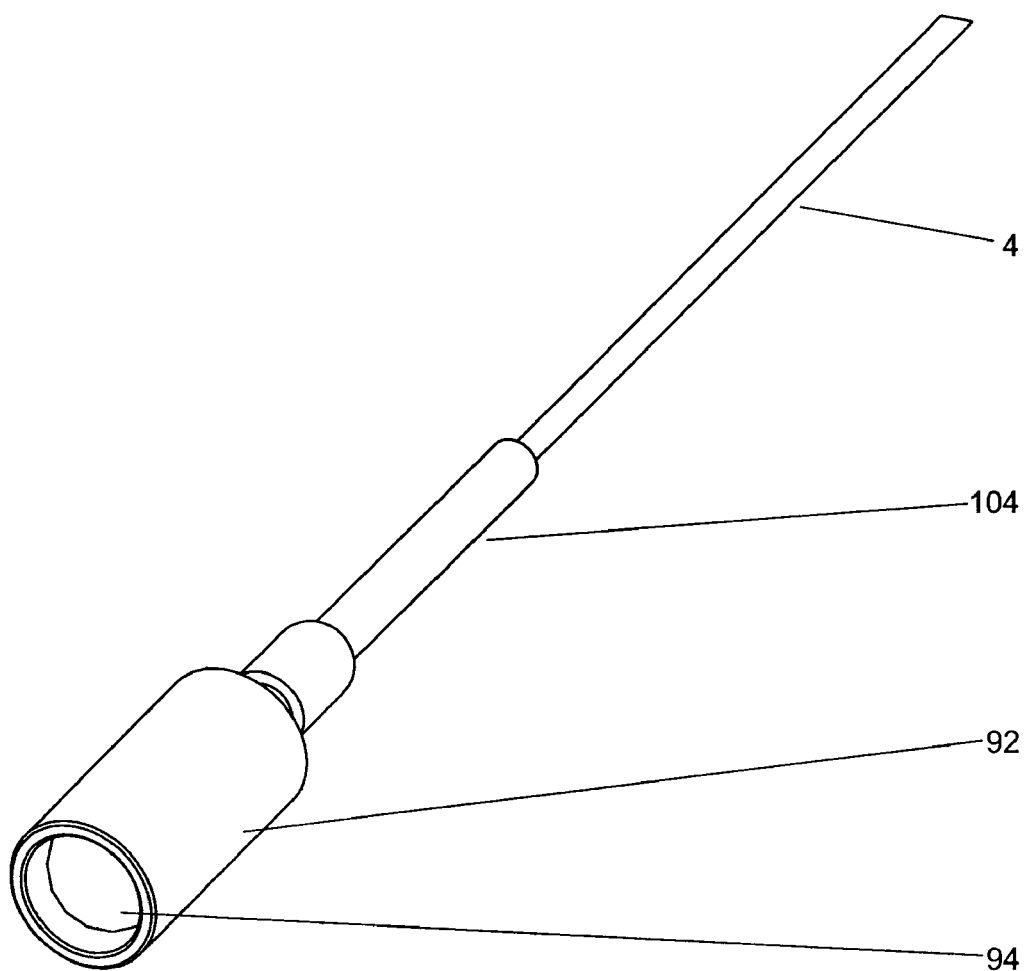
FIG. 13 is an isometric view of an optical fibre which extends into the assembly.
Figure 14:
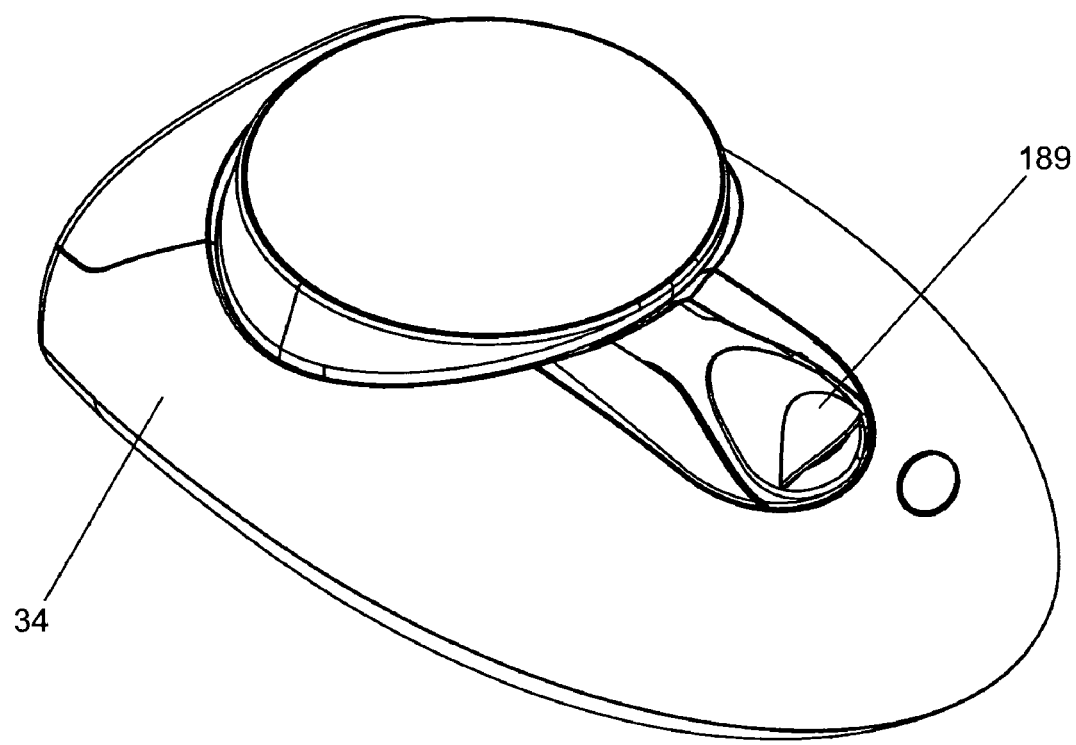
FIG. 14 shows the assembled apparatus with the cover in place.

The arm 138 also carries an upper holder 182 which is releasably snap-fitted onto the upper arm 138 by a mounting arrangement similar to that provided between the table 74 and the lower holder 114. Above the central portion of the holder 182 there is provided a roof prism 184 which extends into a cavity in the upper arm 138 and is attached to the latter either by an adhesive or by means of a clamping mechanism. The roof prism 184 has a lower face which is in registry with an elongate window 186 in the upper holder 182. The window 186 is, in turn, in registry with an upper glass plate 188 which is attached to the underside of the holder 182, and which carries a hydrophobic coating of (for example) DuPont's Teflon AF on its underside. A handling assembly lid 189 is attached to the top of the arm 138, and is shown in FIGS. 12-14. As can be seen from FIG. 14, the lid 189 includes a handle portion 190 to enable a user to raise or lower the upper arm, and a hole 192 in registry the slotted head 170.

Figure 15:
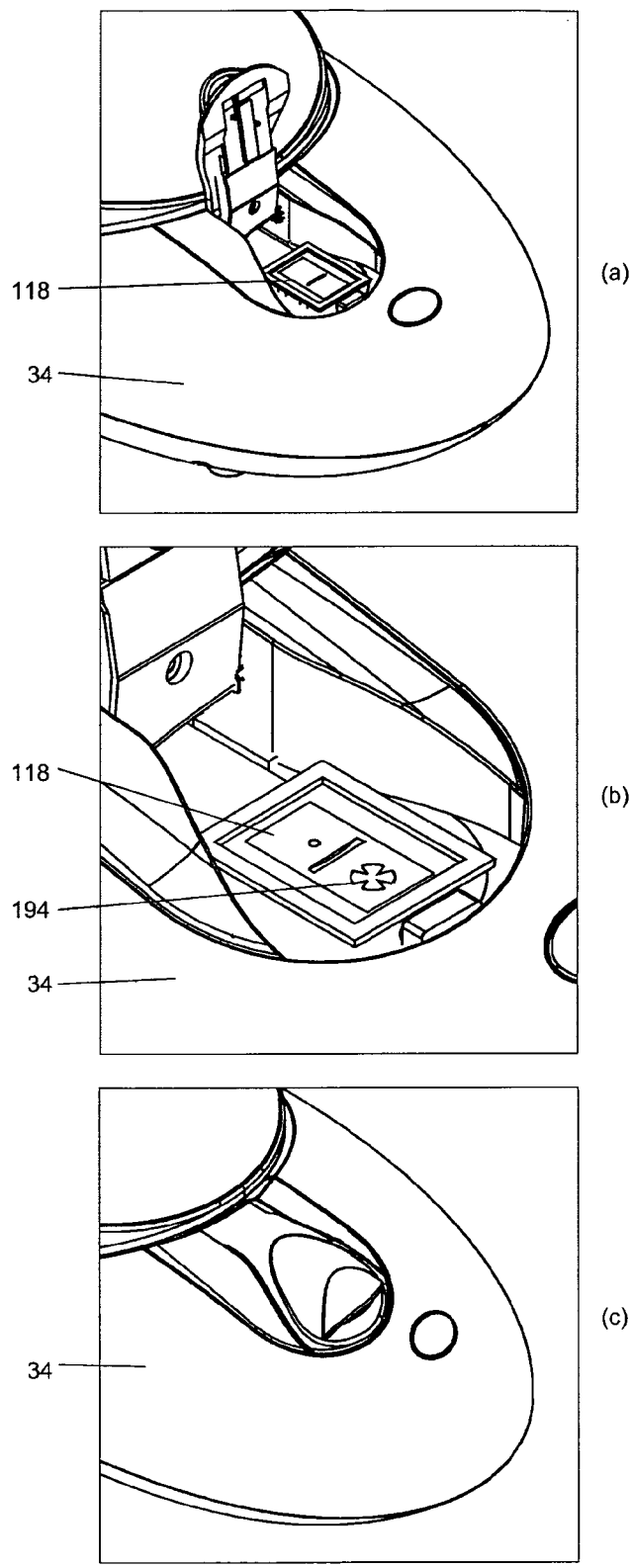
FIGS. 15a-15c are a sequence of frames showing various stages in the operation of the sample handling assembly (the views of the apparatus being shown at a reduced scale)
Figure 16:
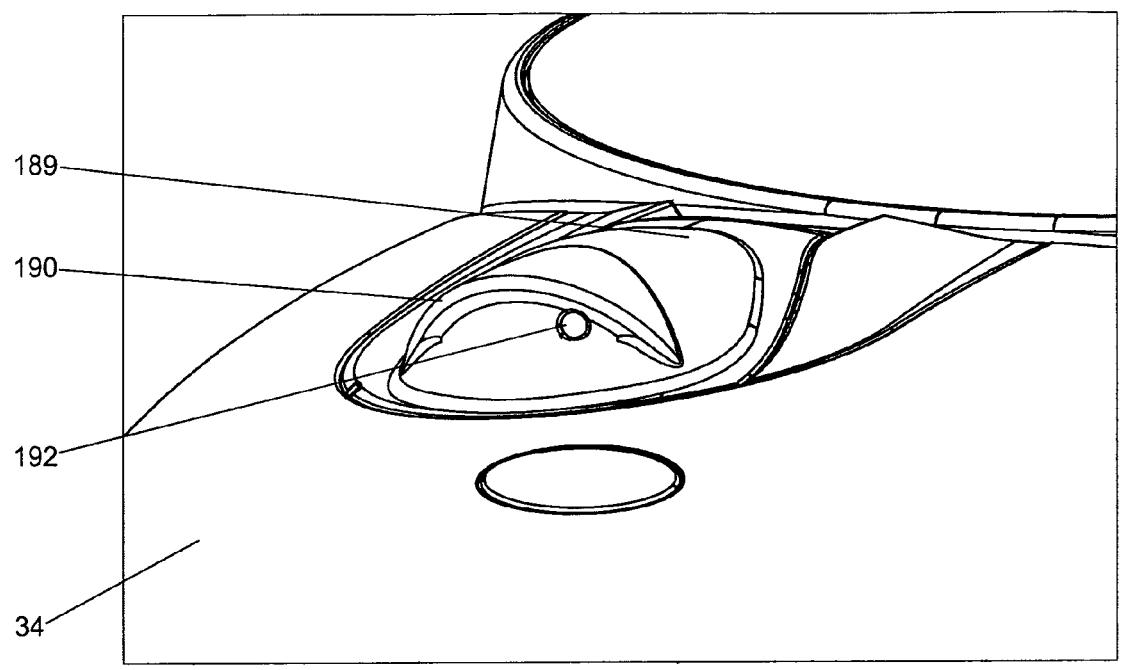
FIG. 16 is an enlarged view of the apparatus.

To place a sample on the apparatus for measurement, the user must first open the lid 189 of the liquid handling assembly 10, as shown in FIG. 15(a). This causes the upper arm 138 to pivot about the hinge pin 136, and thus raises the upper arm 138 and the elements attached to it (including the plate 188) away from the table 74 to expose the upper surface of the plate 118 as shown in FIGS. 13(a) and 13(b).

The user then places a sample droplet 194 on the cross 122 on the upper surface of the plate 118 (as shown in FIG. 15(b)). During these steps, the safety interlock system provided by the Hall Effect sensor 178 and the magnet 108 prevents the operation of the xenon lamp module 1. This is because the switch is connected to the PCB 16 which is so configured as to prevent the operation of the lamp module unless an enabling signal is received from the switch, and this does not happen when the lid is open.

The user then shuts the lid 189 (FIG. 13(c)) so that the droplet is squashed between the upper and lower glass plates. The gap between the plates corresponds to the sample path length is pre-set at one millimeter. This is the distance Z indicated in FIG. 8. This distance is maintained by the pin 162 which is initially in its extended position. Since the surfaces of the plates 118 and 188 in contact with the sample are hydrophobic the integrity of the sample is maintained, the sample taking the form of a bead which spreads out over the plates whilst compressed. The closing of the lid 189 also causes the switch 178 to close so that the lamp module 1 is enabled.

The lamp then fires a single pulse of light which is conveyed to the monochromater 8 (and along optical fibre 4 to the sample handling assembly 10). The pulse passes from the end of the optical fibre 4 and through the ball lens 94 which collimates the light from the pulse to a desired diameter (1-5 millimeters) beam. The light then travels through the lower plate 118, the sample compressed between the plates, the upper plate 188 and into the prism 184 which reflects the light back down through the plates (at a region where the sample has not reached) and into the lens 96 to be conveyed by the optical fibre 12 to the monochromater 8. The light fed directly to the monochromater along the fibre 6 constitutes a reference channel, the light from the fibre 12 a measurement channel. The monochromater processes the light from both channels simultaneously: within the monochromater, the light is directed onto a diode array sensor via a series of mirrors and a diffraction grating.

If a signal is received through the measurement channel this confirms that the prism 184 is in place and that measurement can proceed.

The apparatus then fires an appropriate number of pulses from the lamp module 1 to ensure that a strong return signal (with a reasonable signal to noise ratio), is obtained by the diode array sensor. A measurement is then taken at the 1 millimeter pathlength position.

The signal that has been received by the sensor is then analysed by the PCB 16.

The PCB then sends an actuating signal to the motor 148 causing the latter to retract the pin 162 into the arm 138. This allows the lid to move downwards under gravity allowing the further pin 164 to rest against the lower glass plate 118, thus reducing the path length to between 0.1 and 0.3 millimeters, depending on the position of the pin 164 as governed by the cam 168. The initial check and measurement processes are then repeated with a reduced gap, and the motor 148 then operates for a second time allowing the pin 162 to return to its original, extended position, and hence to increase the path length to 1 millimeter.

The type of analysis employed on the signals obtained by the monochromater is already known, and is not therefore described in detail.

After the user has taken the measurements mentioned above, the user raises the lid 189 of the sample handling assembly 10, thus disengaging the interlock (Hall Effect switch 178 and magnet 108), to ensure that the system is now non-operational and no bright UV flashes can be emitted by the xenon lamp.

If the user wishes to keep the sample for further use, it may be removed using a pipette. Alternatively, the sample may be removed using a laboratory wipe or cloth.

Any small residual traces can be removed by wiping the top and bottom plates with an absorbent wipe (ideally alcohol based).

The upper and lower plates of the sample handling assembly 10 may be renewed periodically by the user, in the event of the deterioration of either hydrophobic coating. The glass plates are permanently fixed within the holders 114 and 182, which can be unclipped from the table 74 or (as the case may be) arm 138 and replaced with identical holders which carry replacement, coated plates.

If the holders are replaced, it is desirable to be able to calibrate the system. To that end, a calibration fluid could be applied to the lower glass plate in the same manner as an ordinary sample. The lid 189 can then be closed and the appropriate programme run by the user to calibrate the instrument. To do this effectively the user may be required to adjust the pin that controls the 0.1 millimeter-0.3 millimeter path length position (i.e. pin 164). The fine tuning of the pin position is done by the cam 168 of the actuator, by inserting a flat screwdriver through the hole 192 in the front of the lid 189. If this is required, the user will be prompted to do this by the instrument's display.

Figure 17:
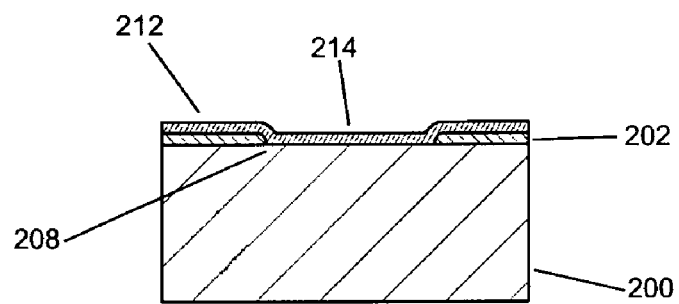
FIG. 17 is a sectional end view of part of a modified version of lower plate for the assembly.
Figure 18:
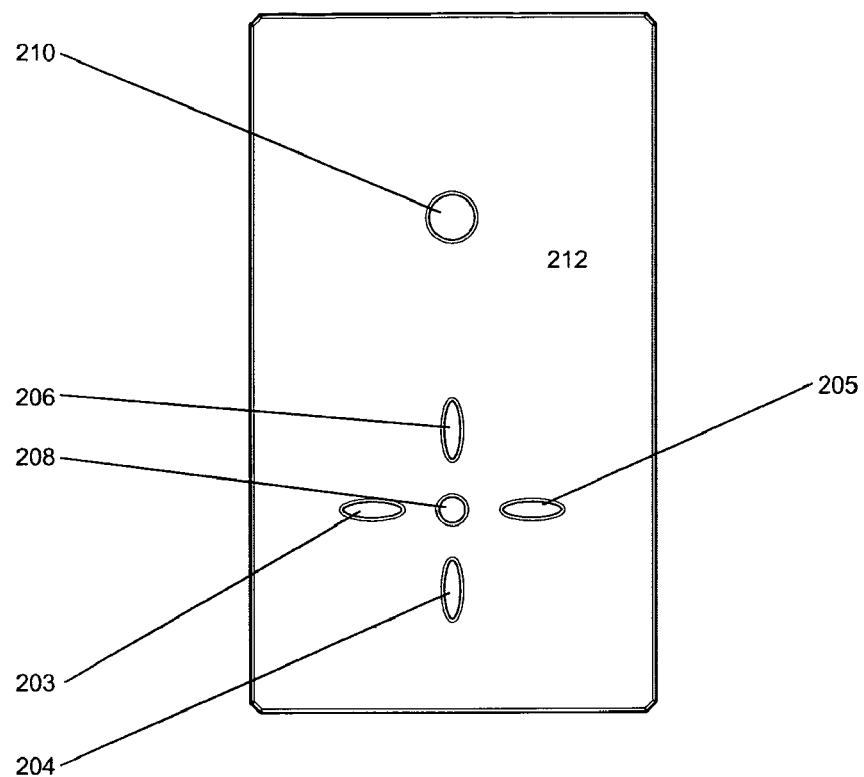
FIG. 18 is a plan view of the plate.

FIGS. 17 and 18 show an alternative type of plate for use in place of plate 118.

The alternative type of plate has a glass substrate 200 onto which a black or grey ink has been screen printed and dried to leave an opaque layer 202 of a thickness of about 20-40 microns. The ink layer 202 includes elongated apertures 203-206 which define a cross marking having a similar purpose to the marking 122, and which extend radially relative to a central, circular aperture 208 about which the elongated apertures 203-206 are equiangularly arranged. The aperture 208 corresponds to the position at which the upwardly direction portion of the beam passes through the plate. A further circular aperture 210, in the coating 202 is provided at the position of the return leg of the beam. The diameter of the aperture 208 is approximately 1.3 mm.

The Teflon AF coating 212 is applied to the upper surface of the layer 202, the aperture 208 in which defines a very shallow well 214, into which the droplet will preferentially extrude as the upper plate closes upon it. The well thus provides a means for centering a sample droplet should the latter not be accurately placed on the plate.

The invention claimed is:

1. Apparatus for analysing a liquid sample, the apparatus comprising a beam generator for generating a beam of electromagnetic radiation, a detector for detecting electromagnetic radiation from said generator after the electromagnetic radiation has interacted with the sample, sample retaining elements for releasably retaining the sample in the path of the beam, wherein the sample retaining elements comprise a surface on which the sample is, in use supported, the surface being one of a pair of such surfaces of the sample-retaining elements between which, in use, a sample being analysed is sandwiched, the sample being situated in a gap between two surfaces, wherein at least one of said surfaces is transparent to said electromagnetic radiation, the beam, in use, travelling through that surface and across the gap, wherein at least one of those surfaces is movable so that the surfaces have an open condition in which the sample is applied to or removed from at least one of the two surfaces and in a closed condition in which the sample is sandwiched between the surfaces, and wherein the surfaces are hydrophobic.

2. Apparatus according to claim 1, in which the apparatus is operable to generate a beam of electromagnetic radiation, and to define a path for said beam which path passes through at least a part of a sample being analysed.

3. Apparatus according to claim 2, in which the beam generator comprises a source of light.

4. Apparatus according to claim 3, in which the beam generator comprises a source of ultraviolet light.

5. Apparatus according to claim 1, in which the beam travels across said gap in a direction substantially perpendicular to said gap.

6. Apparatus according to claim 1, in which the surfaces are positioned one above the other and are substantially parallel to each other when in the closed condition.

7. Apparatus according to claim 6, in which the upper of said surfaces is mounted on a pivotal arm assembly so arranged that pivoting of the arm assembly moves the upper surface to achieve said movement between the open and closed conditions.

8. Apparatus according to claim 6, in which the surfaces are constituted by hydrophobic coatings on upper and lower members.

9. Apparatus according to claim 6, in which the lower member is transparent to allow the passage into the sample of the beam from the beam generating means, said beam being incident on the lower member from underneath.

10. Apparatus according to claim 6, in which the lower member comprises a plate.

11. Apparatus according to claim 6, in which the apparatus includes an overhead reflector for reflecting the beam that has passed through the sample back to a region beneath the underside of the lower member.

12. Apparatus according to claim 11, in which the reflector comprises a prism.

13. Apparatus according to claim 12, in which the prism is spaced from the member on which the upper surface is provided.

14. Apparatus according to claim 12, in which the upper surface is constituted by a hydrophobic coating on an upper transparent plate situated beneath said reflector.

15. Apparatus according to claim 14, in which the plates are removable.

16. Apparatus according to claim 1, in which the apparatus includes an interlock operable to permit operation of the beam generating means only when the surfaces are in their closed condition.

17. Apparatus according to claim 16, in which the interlock comprises a magnet and a magnetic switch, which are brought into and out of operative engagement with each other by the opening and closing of the surface.

18. Apparatus according to claim 17, in which the magnet is fixed relative to one of the surfaces, the switch being fixed relative to the other.

19. Apparatus according to claim 17, in which the switch comprises a Hall Effect Sensor.

20. Apparatus according to claim 1, in which the beam generator and detector each includes a respective light guide, respectively for emitting the beam towards the sample and receiving the beam transmitted through the sample.

21. Apparatus according to claim 20, in which both light guides are on the same side of one of the surfaces.

22. Apparatus according to claim 1, in which each light guide comprises a respective optical fibre.

23. Apparatus according to claim 1, in which the apparatus includes a moveable stop for defining a minimum distance between the surfaces, when in their closed condition, and a drive for extending and/or retracting the stop automatically to vary the distance in the course of a succession of measurements performed on the sample.

24. Apparatus according to claim 23, in which the distance between the surfaces, when in their closed condition, is not more than 0.1 mm, the diameter of the beam being of the order of 1-5 millimeters.

25. Apparatus according to claim 24, in which the diameter of the beam is 1.6 mm.

26. A method of performing photometric or spectrophotometric analysis of a liquid sample of a volume not more than five microlitres, the method comprising the steps of placing the sample on one of a pair of hydrophobic surfaces so as to be supported on said surface, when said surfaces are in an open condition, moving at least one of the surfaces until the surfaces are in a closed condition, in which the surfaces oppose each other across a gap and the sample is sandwiched between two surfaces, passing a beam of electromagnetic radiation through one of the surfaces and through the sample and hence across the gap between the surfaces, and analysing the beam after it has passed through the sample, wherein the beam, after having passed through the sample, is reflected towards a detector for analysing the beam, by a prism situated on the opposite side of one of the surfaces from the sample.

27. A method according to any of claim 26, wherein the beam has a diameter of the order of 1-5 millimeters and the sample has a cross sectional area which is at least as large as that of the beam.

28. Apparatus for analysing a liquid sample, the apparatus comprising a beam generator for generating a beam of electromagnetic radiation, a detector for detecting electromagnetic radiation from said generator after the electromagnetic radiation has interacted with the sample, a sample retaining element for releasably retaining the sample in the path of the beam, wherein the sample retaining element comprises a hydrophobic surface on which the sample is, in use, supported, wherein the surface is one of a pair of such surfaces between which, in use, a sample being analysed is sandwiched, at least one of the surfaces is movable so that the surfaces have an open condition in which a sample is applied to or removed from at least one of the surfaces and a closed condition in which the sample is sandwiched between the two surfaces and wherein the apparatus includes an interlock operable to permit operation of the beam generator only when the surfaces are in their closed condition.

29. Apparatus for analysing a liquid sample, the apparatus comprising a beam generator for generating a beam of electromagnetic radiation, a detector for detecting electromagnetic radiation from said beam generator after the electromagnetic radiation has interacted with the sample and a sample-retaining element for releasable retaining the sample in the path of the beam, wherein the sample-retaining element comprises a hydrophobic surface on which the sample, in use, is supported, wherein the surface is one of a pair of such surfaces between which, in use, a sample being analysed is sandwiched, wherein at least one of the surfaces is movable so that the surfaces have an open condition in which a sample is applied to or removed from at least one of the surfaces, and a closed condition in which the sample is sandwiched between the two surfaces and wherein the apparatus includes a movable stop for defining a minimum distance between the surfaces, when in their closed condition, and a drive for at least one of extending and retracting the stop, automatically to vary the distance in the course of a succession of measurements performed on the sample.

\* \* \* \* \*